US010126308B2

(12) United States Patent
Borges et al.

(10) Patent No.: US 10,126,308 B2
(45) Date of Patent: Nov. 13, 2018

(54) METHODS FOR ASSESSING BIOSPECIMEN INTEGRITY

(71) Applicant: Arizona Board of Regents on behalf of Arizona State University, Scottsdale, AZ (US)

(72) Inventors: Chad Borges, Avondale, AZ (US); Joshua Jeffs, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/469,867

(22) Filed: Mar. 27, 2017

(65) Prior Publication Data

US 2017/0234885 A1 Aug. 17, 2017

Related U.S. Application Data

(63) Continuation-in-part of application No. 15/119,676, filed as application No. PCT/US2015/015472 on Feb. 11, 2015.

(60) Provisional application No. 61/940,752, filed on Feb. 17, 2014.

(51) Int. Cl.
*G01N 33/68* (2006.01)
*G01N 33/49* (2006.01)
*H01J 49/00* (2006.01)
*H01J 49/16* (2006.01)

(52) U.S. Cl.
CPC ........ *G01N 33/6848* (2013.01); *H01J 49/165* (2013.01); *G01N 33/49* (2013.01); *G01N 2333/76* (2013.01); *G01N 2440/34* (2013.01); *G01N 2560/00* (2013.01); *Y10T 436/24* (2015.01)

(58) Field of Classification Search
CPC ............... G01N 33/68; G01N 33/6815; G01N 33/6848; G01N 33/49; G01N 2333/76; G01N 2333/775; G01N 2440/34; G01N 2560/00; H01J 49/00; H01J 49/0036; H01J 49/165; Y10T 436/18; Y10T 436/24
USPC ............... 436/63, 86, 88, 89, 119, 173, 904; 435/29
See application file for complete search history.

(56) References Cited

U.S. PATENT DOCUMENTS 8,669,111 B2 3/2014 Rehder et al.
2002/0068814 A1 6/2002 Smith et al.
2007/0161555 A1 7/2007 Yanagita
2009/0137063 A1* 5/2009 Skold .................... G01N 33/68 436/501
2010/0183607 A1* 7/2010 Hazen ............... G01N 33/6893 424/133.1
2010/0267074 A1* 10/2010 Bar-Or .................. G01N 33/50 435/29
2011/0256105 A1 10/2011 Marban et al.
2013/0177551 A1 7/2013 Hazen et al.
2013/0296260 A1 11/2013 Kitamura et al.
2017/0010278 A1 1/2017 Borges et al.

FOREIGN PATENT DOCUMENTS

WO 2015123338 A2 8/2015

OTHER PUBLICATIONS

Rael et al. The Journal of Trauma, Injury, Infection and Critical Care, vol. 66, No. 1, Jan. 2009, pp. 76-81.*
Peters, T. et al., "All About Albumin: Biochemistry, Genetics, and Medical Applications", Dec. 1995, Academic Press, San Diego.
Poste, G. et al., "The national biomarker development alliance: confronting the poor productivity of biomarker research and development", Expert Review of Molecular Diagnostics, Feb. 2015 (available online Nov. 2014), 15(2), pp. 211-218.
Rael, L. et al., "The effect of storage on the accumulation of oxidative biomarkers in donated packed red blood cells", Journal of Trauma, Jan. 2009, 66(1), pp. 76-81.
Rai, A. et al., "HUPO Plasma Proteome Project specimen collection and handling: towards the standardization of parameters for plasma proteome samples", Proteomics, Aug. 2005, 5(13), pp. 3262-3277.
Ransohoff, D. et al., "Sources of bias in specimens for research about molecular markers for cancer", Journal of Clinical Oncology, Feb. 2010 (available online Dec. 2009), 28(4), pp. 698-704.
Rehder, D. et al., "Cysteine sulfenic Acid as an Intermediate in Disulfide Bond Formation and Nonenzymatic Protein Folding", Biochemistry, Jul. 2010, 49(35), pp. 7748-7755.
Rifai, N. et al., "An appeal to medical journal editors: The need for a full description of laboratory methods and specimen handling in clinical study reports", American Journal of Hematology, Apr. 2012 (available online Jan. 2012), 87(4), pp. 347-348.
Rifai, N. et al., "An appeal to medical journal editors: The need for a full description of laboratory methods and specimen handling in clinical study reports", Clinica Chimica Acta, Apr. 2012 (available online Jan. 2012), 413(7-8), pp. 653-655.
Rifai, N. et al., "An appeal to medical journal editors: The need for a full description of laboratory methods and specimen handling in clinical study reports", Clinical Biochemistry, Feb. 2012 (Jan. 2012), 45(3), pp. 185-186.

(Continued)

*Primary Examiner* — Maureen Wallenhorst
(74) *Attorney, Agent, or Firm* — Gavin J. Milczarek-Desai; Quarles & Brady LLP

(57) ABSTRACT

Methods for quantifying biospecimen sample integrity using oxidation. Embodiments include assessing ex vivo oxidation of a biospecimen sample by quantifying a difference in protein oxidation of the biospecimen sample in comparison to protein oxidation of a portion of the biospecimen sample intentionally incubated to cause oxidation to hit its maximum value. The difference in a level of oxidation in the biospecimen sample and the portion of the biospecimen sample is then inversely proportional to the degree of ex vivo oxidation.

8 Claims, 14 Drawing Sheets

Specification includes a Sequence Listing.

(56) References Cited

OTHER PUBLICATIONS

Rifai, N. et al., "An appeal to medical journal editors: the need for a full description of laboratory methods and specimen handling in clinical study reports", Clinical Chemistry and Laboratory Medicine, Mar. 2012, 50(3), pp. 411-413.
Rifai, N. et al., "An appeal to medical journal editors: the need for a full description of laboratory methods and specimen handling in clinical study reports", Clinical Chemistry, Mar. 2012 (available online Feb. 2012), 58(3), pp. 483-485.
Rifai, N. et al., "An Appeal to Medical Journal Editors: The Need for a Full Description of Laboratory Methods and Specimen Handling in Clinical Study Reports", Scandinavian Journal of Clinical & Laboratory Investigation, Apr. 2012 (available online Feb. 2012), 72(2), pp. 89-91.
Rifai, N. et al., "An appeal to medical journal editors: the need for a full description of laboratory methods and specimen handling in clinical study reports", Transfusion, Jun. 2012 (available online Mar. 2012), 52(6), pp. e17-e19.
Rifai, N. et al., "An appeal to medical journal editors: the need for a full description of laboratory methods and specimen handling in clinical study reports. Statement by the Consortium of Laboratory Medicine Journal Editors", Annals of Clinical Biochemistry, Mar. 2012, 49(2), pp. 105-107.
Robb, J. et al., "Documenting Biospecimen Conditions in Reports of Studies", JAMA, Aug. 2008, 300(6), pp. 650-651.
Sattler, W. et al., "Cholesterylester hydroperoxide reducing activity associated with isolated high- and low-density lipoproteins", Free Radical Biology and Medicine, Mar. 1995, 18(3), pp. 421-429.
Schully, S. et al., "Leveraging biospecimen resources for discovery or validation of markers for early cancer detection", Journal of the National Cancer Institute, Apr. 2015 (available online Feb. 2015), 4(1), article djv012, doi:10.1093/jnci/djv012.
Segrest, J. et al., "A Detailed Molecular Belt Model for Apolipoprotein A-I in Discoidal High Density Lipoprotein", Journal of Biological Chemistry, Nov. 1999, 274(45), pp. 31755-31758.
Sela, M. et al., "Reductive Cleavage of Disulfide Bridges in Ribonuclease", Science, Apr. 1957, 125(3250), pp. 691-692.
Sourvinou, I. et al., "Quantification of circulating miRNAs in plasma: effect of preanalytical and analytical parameters on their isolation and stability", Journal of Molecular Diagnostics, Nov. 2013 (available online Aug. 2013), 15(6), pp. 827-834.
Tuck, M. et al., "Standard Operating Procedures for Serum and Plasma Collection: Early Detection Research Network Consensus Statement Standard Operating Procedure Integration Working Group", Journal of Proteome Research, Jan. 2009 (available online Dec. 2008), 8(1), pp. 113-117.
Turell, L. et al., "Oxidation of the albumin thiol to sulfenic acid and its implications in the intravascular compartment", Brazilian Journal of Medical and Biological Research, Apr. 2009, 42(4), pp. 305-311.
Turell, L. et al., "Reactivity of Sulfenic Acid in Human Serum Albumin", Biochemistry, Jan. 2008 (available online Dec. 2007), 47(1), pp. 358-367.
Turell, L. et al., "Sulfenic acid—A key intermediate in albumin thiol oxidation", Journal of Chromatography B, Oct. 2009 (available online Mar. 2009), 877(28), pp. 3384-3392.
Vaught, J. et al., "Biospecimens and biorepositories: from afterthought to science", Cancer Epidemiology, Biomarkers & Prevention, Feb. 2012, 21(2), pp. 253-255.
Vaught, J. et al., "The evolution of biobanking best practices", Clinica Chimica Acta, Oct. 2012 (available online May 2012), 413(19-20), pp. 1569-1575.
Vaught, J. et al., "What Are Three Actionable Strategies to Improve Quality in Biomedical Research", Biopreservation and Biobanking, Sep. 2010, 8(3), pp. 121-125.
Von Eckardstein, A. et al., "Site-specific methionine sulfoxide formation is the structural basis of chromatographic heterogeneity of apolipoproteins A-I, C-II, and C-III", Journal of Lipid Research, Sep. 1991, 32(9), pp. 1465-1476.
Wang, S. et al., "A sensitive and specific ELISA detects methionine sulfoxide-containing apolipoprotein A-I in HDL", Journal of Lipid Research, Mar. 2009 (published Oct. 2008), 50(3), pp. 586-594.
White, F. et al., "Regeneration of native secondary and tertiary structures by air oxidation of reduced ribonuclease", Journal of Biological Chemistry, May 1961, 236(5), pp. 1353-1360.
Wolff S. et al., "Glucose autoxidation and protein modification. The potential role of 'autoxidative glycosylation' in diabetes", Biochemical Journal, Jul. 1987, 245(1), pp. 243-250.
Woodward, M .et al., "Association between both lipid and protein oxidation and the risk of fatal or non-fatal coronary heart disease in a human population", Clinical Science, Jan. 2009, 116(1), pp. 53-60.
Wu, Z. et al., "The refined structure of nascent HDL reveals a key functional domain for particle maturation and dysfunction", Nature Structural & Molecular Biology, Aug. 2007, 14(9), pp. 861-868.
Yamada, A. et al., "Technical factors involved in the measurement of circulating microRNA biomarkers for the detection of colorectal neoplasia", PLoS One, Nov. 2014, 9(11), article e112481, 8 pages, https://doi.org/10.1371/journal.pone.0112481.
Yassine, H. et al., "Mass spectrometric immunoassay and MRM as targeted MS-based quantitative approaches in biomarker development: potential applications to cardiovascular disease and diabetes", Proteomics Clinical Applications, Aug. 2013 (available online May 2013), 7(7-8), pp. 528-540.
Non-Final Office Action, U.S. Appl. No. 15/119,676, dated Mar. 20, 2018.
International Search Report and Written Opinion for PCT/US 15/15472 filed on Nov. 2, 2015.
Betsou et al., Identification of evidence based biospecimen qualitycontrol tools: a report of the International Society for Biological and Environmental Repositories (ISBER) Biospecimen Science Working Group. The Journal of Molecular Diagnostics, 2013, 15(1):3-16.
Labaer et al., Improving international research with clinical specimens: 5 achievable objectives. Journal of Proteome Research, 2012, 11(12):5592-5601.
Blow, Biobanking: freezer burn. Nature Methods, 2009;6(2):173-177.
Bravo et al., Effect of temperature on plasma freezing under industrial conditions. Pharmeuropa Scientific Notes, 2006, 1:31-35.
European Pharmacopoeia 5th Edition, Human plasma for fractionation, monograph 0853, 2005, pp. 1746-1747, Strasbourg, France: Council of Europe.
Boys et al., Protein oxidative modifications during electrospray ionization: solution phase electrochemistry or corona discharge induced radical attack? Analytical chemistry, 2009, 81(10):4027-4034.
Borges et al., Elevated Plasma Albumin and Apolipoprotein A-I Oxidation under Suboptimal Specimen Storage Conditions. Molecular and Cellular Proteomics, 2014, 13(7):1890-1899.
Roeser et al., Oxidative protein labeling in mass-spectrometry-based proteomics. Analytical and Bioanalytical Chemistry, 2010, 397(8):3441-3455.
Anantharamaiah, G. et al., "Effect of oxidation on the properties of apolipoproteins A-I and A-II", Journal of Lipid Research, Mar. 1988, 29(3), pp. 309-318.
Andre, F. et al., "Biomarker studies: a call for a comprehensive biomarker study registry", Nature Reviews Clinical Oncology, Mar. 2011, 8(3), pp. 171-176.
Anfinsen, C. et al., "Studies on the Reduction and Re-formation of Protein Disulfide Bonds", The Journal of Biological Chemistry, May 1961, 236(5), pp. 1361-1363.
Anfinsen, C. et al., "The kinetics of formation of native ribonuclease during oxidation of the reduced polypeptide chain", PNAS, Sep. 1961, 47(9), pp. 1309-1314.
Antman, E. et al., "The TIMI Risk Score for Unstable Angina/Non—ST Elevation MI: A Method for Prognostication and Therapeutic Decision Making", JAMA, Aug. 2000, 284(7), pp. 835-842.
Ayache, S. et al., "Effects of storage time and exogenous protease inhibitors on plasma protein levels", American Journal of Clinical Pathology, Aug. 2006, 126(2), pp. 174-184.

(56) References Cited

OTHER PUBLICATIONS

Barden, A. et al., "Minimizing artifactual elevation of lipid peroxidation products (F2-isoprostanes) in plasma during collection and storage", Analytical Biochemistry, Mar. 2014 (available online Dec. 2013), vol. 449, pp. 129-131.
Bar-Or, D. et al., "Cysteinylation of maternal plasma albumin and its association with intrauterine growth restriction", Prental Diagnosis, Mar. 2005, 25(3), pp. 245-249.
Bar-Or, D. et al., "Heterogeneity and oxidation status of commercial human albumin preparations in clinical use", Critical Care Medicine, Jul. 2005, 33(7), pp. 1638-1641.
Betsou, F. et al., "Assays for Qualification and Quality Stratification of Clinical Biospecimens Used in Research: A Technical Report from the ISBER Biospecimen Science Working Group", Biopreservation and Biobanking, Oct. 2016 (available online Apr. 2016), 14(5), pp. 398-409.
Betsou, F. et al., "Human Biospecimen Research: Experimental Protocol and Quality Control Tools", Cancer Epidemiology, Biomarkers & Prevention, Apr. 2009 (available online Mar. 2009), 18(4), pp. 1017-1025.
Betsou, F. et la., "Long-term stability of coagulation variables: Protein S as a biomarker for preanalytical storage-related variations in human plasma", Thrombosis and Haemostasis, Jun. 2009, 101(6), pp. 1172-1175.
Blanco, R. et al., "Diurnal variation in glutathione and cysteine redox states in human plasma", The American Journal of Clinical Nutrition, Oct. 2007, 86(4), pp. 1016-1023.
Borges, C. et al., "Building multidimensional biomarker views of type 2 diabetes on the basis of protein microheterogeneity", Clinical Chemistry, May 2011 (available online Mar. 2011), 57(5), pp. 719-728.
Borges, C. et al., "Impact of Artifactual Ex Vivo Oxidation on Biochemical Research", Oxidative Stress: Diagnostics, Prevention, and Therapy vol. 2 (eds. Hepel and Andreescu), Oct. 2015, Chapter 16, pp. 375-413.
Bowry, V. et al., "High density lipoprotein is the major carrier of lipid hydroperoxides in human blood plasma from fasting donors", PNAS USA, Nov. 1992, 89(21), pp. 10316-10320.
Brot, N. et al., "Biochemistry of methionine sulfoxide residues in proteins", Biofactors, Jun. 1991, 3(2), pp. 91-96.
Center for Disease Control and Prevention, "National Health and Nutritition Examination Survey 2005-2006", Standard Biochemistry Profile, variable of interest LBDSALSI (albumin in refrigerated serum, g/L), published Mar. 2008, <https://wwwn.cdc.gov/nchs/nhanes/search/datapage.aspx?Component=Laboratory &CycleBeginYear=2005> (last accessed May 29, 2018).
Chaigneau, C. et al., "Serum biobank certification and the establishment of quality controls for biological fluids: examples of serum biomarker stability after temperature variation", Clinical Chemistry and Laboratory Medicine, 2007, 45(10), pp. 1390-1395.
Compton, C., "Getting to personalized cancer medicine: Taking out the garbage", Cancer, Oct. 2007 (available online Aug. 2007), 110(8), pp. 1641-1643.
Costello, M. et al., "Discovery and characterization of artifactual mutations in deep coverage targeted capture sequencing data due to oxidative DNA damage during sample preparation", Nucleic Acids Research, Apr. 2013 (available online Jan. 2013), 41(6), article e67, 12 pages, doi:10.1093/nar/gks1443.
De Jager, W. et al., "Prerequisites for cytokine measurements in clinical trials with multiplex immunoassays", BMC Immunology, Sep. 2009, vol. 10, article 52, 11 pages, doi:10.1186/1471-2172-10-52.
Early Detection Research Network, "The Early Detection Research Network (EDRN) Standard Operating Procedure (SOP) for Collection of EDTA Plasma", https://edrn.nci.nih.gov/resources/standard-operating-procedures/standard-operating-procedures/plasma-sop.pdf, version submitted dated Oct. 29, 2011, obtained from archive.org (https://web.archive.org/web/20111029104355/http://edrn.nci.nih.gov/resources/standard-operating-procedures/standard-operating-procedures/plasma-sop.pdf).
Early Detection Research Network, "The Early Detection Research Network (EDRN) Standard Operating Procedure (SOP) for Collection of Serum", https://edrn.nci.nih.gov/resources/standard-operating-procedures/standard-operating-procedures/serum-sop.pdf, version submitted dated Oct. 29, 2011, obtained from archive.org (https://web.archive.org/web/20111029104358/https://edrn.nci.nih.gov/resources/standard-operating-procedures/standard-operating-procedures/serum-sop.pdf).
Ellervik, C. et al., "Preanalytical variables affecting the integrity of human biospecimens in biobanking", Clinical Chemistry, Jul. 2015 (available online Jun. 2015), 61(7), pp. 914-934.
Engel, K. et al., "National Cancer Institute Biospecimen Evidence-Based Practices: a novel approach to pre-analytical standardization", Biopreservation and Biobanking, Apr. 2014, 12(2), pp. 148-150.
Farrugia, A. et al., "Factor VIII/von Willebrand factor levels in plasma frozen to-30 degrees C in air or halogenated hydrocarbons", Thrombosis Research, Oct. 1992, 68(1), pp. 97-102.
Garner, B. et al., "Oxidation of high density lipoproteins. I. Formation of methionine sulfoxide in apolipoproteins AI and AII is an early event that accompanies lipid peroxidation and can be enhanced by alpha-tocopherol", Journal of Biological Chemistry, Mar. 1998, 273(11), pp. 6080-6087.
Garner, B. et al., "Oxidation of high density lipoproteins. II. Evidence for direct reduction of lipid hydroperoxides by methionine residues of apolipoproteins AI and AII", Journal of Biological Chemistry, Mar. 1998, 273(11), pp. 6088-6095.
Ikeda, et al., "Evaluation of the short-term stability of specimens for clinical laboratory testing", Biopreservation and Biobanking, Apr. 2015, 13(2), pp. 135-143.
Jones, D. et al., "Redox analysis of human plasma allows separation of pro-oxidant events of aging from decline in antioxidant defenses", Free Radical Biology and Medicine, Nov. 2002 (available online Oct. 2002), 33(9), pp. 1290-1300.
Kisand, K. et al., "Impact of cryopreservation on serum concentration of matrix metalloproteinases (MMP)-7, TIMP-1, vascular growth factors (VEGF) and VEGF-R2 in Biobank samples", Clinical Chemistry and Laboratory Medicine, Feb. 2010 (available online Dec. 2009), 49(2), pp. 229-235.
Lengelle, J. et al., "Soluble CD40 ligand as a biomarker for storage-related preanalytic variations of human serum", Cytokine, Nov. 2008 (available online Oct. 2008), 44(2), pp. 275-282.
Lim, M. et al., "Before You Analyze a Human Specimen, Think Quality, Variability, and Bias", Analytical Chemistry, Jan. 2011 (available online Nov. 2010), 83(1), pp. 8-13.
Linde, S. et al., "High-performance liquid chromatography of rat and mouse islet polypeptides: potential risk of oxidation of methionine residues during sample preparation", Journal of Chromatography, 1990, 530(1), pp. 29-37.
Lippi, G. et al., "Preanalytical quality improvement: from dream to reality", Clinical Chemistry and Laboratory Medicine, Jul. 2011 (available online Apr. 2011), 49(7), pp. 1113-1126.
Lippi, G. et al., "Preanalytical variability: the dark side of the moon in laboratory testing", Clinical Chemistry and Laboratory Medicine, 2006, 44(4), pp. 358-365.
Maciejko, J. et al., "Apolipoprotein A-I as a Marker of Angiographically Assessed Coronary-Artery Disease", New England Journal of Medicine, Aug. 1983, vol. 309, pp. 385-389.
Mashima, R. et al., "Reduction of phosphatidylcholine hydroperoxide by apolipoprotein A-I: purification of the hydroperoxide-reducing proteins from human blood plasma", Journal of Lipid Research, Jun. 1998, 39(6), pp. 1133-1140.
McLerran, D. et al., "Analytical Validation of Serum Proteomic Profiling for Diagnosis of Prostate Cancer: Sources of Sample Bias", Clinical Chemistry, Jan. 2008 (available online Dec. 2007), 54(1), pp. 44-52.
McLerran, D. et al., "SELDI-TOF MS Whole Serum Proteomic Profiling with IMAC Surface Does Not Reliably Detect Prostate Cancer", Clinical Chemistry, Jan. 2008 (available online Dec. 2007), 54(1), pp. 53-60.

(56) References Cited

OTHER PUBLICATIONS

Moore, H. et al., "2009 Biospecimen research network symposium: advancing cancer research through biospecimen science", Cancer Research, Sep. 2009 (available online Aug. 2009), 69(17), pp. 6770-6772.

Moore, H. et al., "Biospecimen reporting for improved study quality (BRISQ)", Cancer Cytopathology, Apr. 2011 (available online Mar. 2011), 119(2), pp. 92-101.

Moore, H. et al., "International approaches to advancing biospecimen science", Cancer Epidemiology, Biomarkers and Prevention, May 2011, 20(5), pp. 729-732.

Moriarty, S. et al., "Oxidation of glutathione and cysteine in human plasma associated with smoking", Free Radical Biology and Medicine, Dec. 2003 (available online Nov. 2003), 35(12), pp. 1582-1588.

Mullan, A. et al., "More knocks to the oxidation hypothesis for vascular disease", Clinical Science, Jan. 2009, 116(1), pp. 41-43.

Pankhurst, G. et al., "Characterization of specifically oxidized apolipoproteins in mildly oxidized high density lipoprotein", Journal of Lipid Research, Feb. 2003 (available online Nov. 2002), 44(2), pp. 349-355.

Panzenbock, U. et al., "Formation of methionine sulfoxide-containing specific forms of oxidized high-density lipoproteins", Biochimica Biophysica Acta, Jan. 2005 (available online Nov. 2004), 1703(2), pp. 171-181.

Panzenbock, U. et al., "Oxidation of Methionine Residues to Methionine Sulfoxides Does Not Decrease Potential Antiatherogenic Properties of Apolipoprotein A-I", Journal of Biological Chemistry, Jun. 2000 (available online Apr. 2000), 275(26), pp. 19536-19544.

Park, Y. et al., "Postprandial cysteine/cystine redox potential in human plasma vanes with meal content of sulfur amino acids", Journal of Nutrition, Apr. 2010, 140(4), pp. 760-765.

* cited by examiner

Biotin-YRQSMNGSRSTGCRFGTCTMQKLAHQIYQFTDKNKDGMAPRNKISPQGY-$CO_2H$

SH SH

SEQUENCE I.D. No. 1

Fig. 4

SEQUENCE LISTING

```
<160> NUMBER OF SEQ ID NOS: 1

<210> SEQ ID NO 1
<211> LENGTH: 49
<212> TYPE: PRT
<213> ORGANISM: Artificial Sequence
<220> FEATURE:
<223> OTHER INFORMATION: Oxidation Probe

<400> SEQUENCE: 1

Tyr Arg Gln Ser Met Asn Gly Ser Arg Ser Thr Gly Cys Arg Phe Gly
1               5                   10                  15

Thr Cys Thr Met Gln Lys Leu Ala His Gln Ile Tyr Gln Phe Thr Asp
            20                  25                  30

Lys Asn Lys Asp Gly Met Ala Pro Arg Asn Lys Ile Ser Pro Gln Gly
        35                  40                  45

Tyr
```

METHODS FOR ASSESSING BIOSPECIMEN INTEGRITY

CROSS-REFERENCE TO RELATED APPLICATIONS

This application is a continuation in part of and claims priority to U.S. application Ser. No. 15/119,676, filed on Aug. 17, 2016, which is a U.S. National Phase entry of International Application PCT/US2015/015472, filed on Feb. 11, 2015, claiming the benefit of Provisional Patent Application No. 61/940,752 filed on Feb. 17, 2014.

BACKGROUND

Human cell, tissue, or blood plasma and serum (P/S) samples from clinical studies are often archived by biobanks for future research. Unfortunately, such samples are not intrinsically stable. Pre-analytical handling and storage conditions can have a dramatic impact on sample measurements, potentially rendering results invalid. While acceptable pre-analytical conditions are generally well defined for FDA approved clinical protein assays, they cannot always be optimally predefined for clinical research studies where samples are to be archived for open-ended future research.

Therefore, improvements in methods and systems for quality control tools (e.g., markers and assays) that allow for retrospective assessment of biobanked sample integrity are desirable. Such tools are particularly important as the practice of biobanking increases worldwide. The few markers currently proposed for this purpose are based on an apparent quantitative loss in a particular target protein without consideration of the molecular root cause. Therefore, their use as markers of biospecimen integrity is questionable.

SUMMARY

The embodiments described herein relate to methods and systems for detecting biospecimen or biological sample integrity following pre-analytical sample handling, processing, or storage.

Further embodiments relate to methods for quantifying biospecimen sample integrity using oxidation. Embodiments include assessing ex vivo oxidation of a biospecimen sample by quantifying a difference in protein oxidation of the biospecimen sample in comparison to protein oxidation of a portion of the biospecimen sample intentionally incubated to cause oxidation to hit its maximum value.

Biospecimen integrity, or the preservation of the biological sample's chemical structure and/or conformation is critically important when it comes to ensuring the validity of clinically oriented research. This creates a need for quality control tools (e.g., markers and assays) that allow for retrospective assessment of sample integrity. Such tools are particularly important as the practice of biobanking continues to rise worldwide.

For example, ensuring the quality of archived blood plasma/serum (P/S) samples is generally accepted as an important matter—but one on which consensus is still lacking with regard to how this can best be achieved. In general, however, two well accepted requirements for ensuring biospecimen quality control include 1) optimal pre-analytical handling and storage conditions and 2) sample markers that can retrospectively indicate loss of sample integrity. There are functional definitions for both of these requirements. The few markers currently proposed for the second requirement are based on an apparent quantitative loss (or 'paradoxical' increase) in a particular endogenous target molecule without consideration of the molecular root cause. So, use of existing markers as specific indicators of sample integrity is questionable.

The inventors have identified endogenous markers of sample integrity based directly on the molecular modification of proteins caused by spontaneous oxidation ex vivo. In short, the inventors have observed major changes in protein oxidation over time periods of just days to weeks when samples are stored at −20° C. This is important for two reasons: First, blood P/S samples visually appear frozen at −20° C. but do not actually freeze until −30° C. Second, −20° C. is a common laboratory freezer temperature—e.g., one at which clinical trial samples are often stored temporarily after collection until enough have been collected to ship off for analysis and/or archiving.

All forms of protein oxidation intrinsically alter protein structure and may, therefore, disrupt protein binding characteristics. Since essentially all clinical protein assays are based on measuring target protein binding interactions (i.e., to an antibody, protein, or surface), results for all oxidation susceptible proteins are, in principle, potentially confounded by this problem. The inventors believe that many problems with empirical protein biomarker instability are rooted in spontaneous, artefactual ex vivo protein oxidation.

By way of further example, methods have been developed that provide a simple, inexpensive, rapid LC/MS-based test requiring 10 μL of P/S that provides a representative assessment of the oxidative damage that P/S proteins have incurred due to exposure to the thawed state. In one embodiment, the methods are based on the fact that the relative abundance of S-cysteinylated (oxidized) albumin (S-Cys-Alb) will always increase over time (but to a maximum value) when P/S is handled/stored above its melting point of −30° C. Thus by measuring S-Cys-Alb before and after an intentional incubation period that causes S-Cys-Alb to hit its maximum value, the difference between these values, ΔS-Cys-Alb, is readily interpreted as inversely proportional to the degree of ex vivo oxidation that occurred prior to the first measurement of S-Cys-Alb. Thus, for example, a ΔS-Cys-Alb value of zero would indicate a badly mistreated sample.

These and other aspects will be apparent upon reference to the following detailed description and figures. To that end, any patent and other documents cited herein, are hereby incorporated by reference in their entirety.

BRIEF DESCRIPTION OF THE DRAWINGS

FIG. 4 illustrates a sample peptide probe design for simultaneous detection of two types of artefactual ex vivo protein oxidation (disulfide bond formation and methionine sulfoxidation). The biotin tag serves as an affinity handle for easy extraction of the probe from blood plasma/serum.

DETAILED DESCRIPTION

Figure 1A:
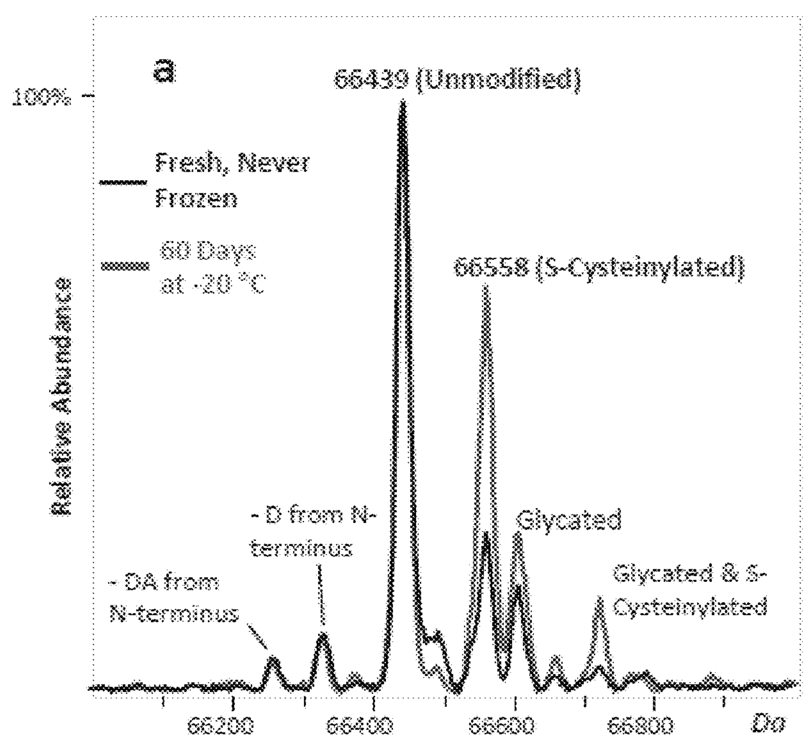
FIGS. 1*a-b* illustrate charge deconvoluted electrospray ionization-mass spectra of albumin and apoA-I from healthy donors showing increasing S-Cysteinylated albumin (SCA) and methionine oxidized apoA-I (MOA1) under less-than-ideal storage conditions. There are 3 methionine residues in apoA-I, permitting up to 3 sulfoxidation events, each of which shifts the mass of the protein up by 16 Da. Red (lighter lines) and black (darker lines) spectra are the same sample, aged as indicated. The heavily oxidized apoA-I sample was obtained from a for-profit biobank after 4 years of storage at unspecified "frozen" storage conditions. A lot-paired sample from a different healthy individual was similarly oxidized (not shown).

Embodiments described herein relate to methods and systems for assessing the preservation of biospecimen chemical structure following pre-analytical sample handling, processing, or storage. These embodiments are utilized via implementation of an analytical methodology combined with proper data analysis, and is potentially useful to anyone interested in assessing the integrity of archived plasma'serum samples. As such, it may be useful to anyone from the individual investigator to large biobanks interested in assessing the integrity of their specimens. Current alternatives include candidate markers. However, none of these markers are widely implemented or accepted as an industry gold standard.

The inventors have discovered markers based directly on the molecular modification of proteins caused by sample oxidation: Under conditions of incomplete P/S sample freezing (including storage at −20° C.) two different forms of oxidation occur spontaneously at protein sulfur atoms—namely, intermolecular disulfide bond formation and methionine sulfoxidation.

For example, such observations have been made on albumin and apolipoprotein Al (apoA-I), respectively, using a very simple form of dilute-and-shoot, trap-and-elute liquid chromatography-mass spectrometry carried out on approximately 0.5 μL of unmodified P/S samples. The reference ranges observed for S-cysteinylated-albumin (SCA) and methionine-oxidized-apoA-I (MOA1) in freshly analyzed samples are low and nonexistent, respectively—even in samples from patients experiencing conditions associated with oxidative stress, e.g., heart attacks. Thus, as oxidized forms of albumin and apoA-I, SCA and MOA1 are useful markers of blood P/S integrity.

This inventive approach has the appeal of providing mechanism based measurements of qualitative changes that occur within proteins due directly to oxidation that occurs when samples are improperly handled and/or stored; in essence, this technology has the unique advantage that it allows one to literally "see" molecular damage that has occurred.

The inventors have recently found that under conditions of incomplete blood plasma/serum (P/S) sample freezing (including storage at −20° C.) two different forms of oxidation occur spontaneously at protein sulfur atoms—namely S-cysteinylation of free cysteine residues (in which the oxidative event is disulfide bond formation) and sulfoxidation of methionine. Most P/S proteins are susceptible to at least one of these forms of oxidation.

Several characteristics make these oxidation based markers useful as a means by which to monitor P/S specimen integrity: 1) SCA and MOA1 are readily quantified in a single assay that uses only about 0.5 μL of P/S. 2) Oxidation of albumin and apoA-I can be prevented by storing P/S samples at about −80° C. or colder. 3) SCA and MOA1 do not appear to be affected by patient health status. 4) The oxidative chemistries of SCA and MOA1 are operational in other proteins and polypeptides. Thus, for rare cases in which the use of SCA or MOA1 may be contraindicated (see below), custom designed surrogate peptide probes based on SCA and MOA1 oxidation chemistry may be fortified into samples at collection to serve as exogenous markers of P/S sample integrity.

Surrogate peptide probe development could be accomplished as follows. For example, one could decide to include a probe, such as the one shown in FIG. 4, within blood collection tubes (much like anticoagulants or protease inhibitors are currently added to different types of blood collection tubes). While the concentration at which the probe will be added can vary, it will likely be somewhere between 1 nanomolar and 1 micromolar. When the sample is to be tested, the cysteine status of the probe will be locked via sample alkylation with maleimide (or other suitable alkylating reagent), then the probe will be extracted by affinity capture with monomeric avidin (or possibly streptavidin or neutravidin) immobilized to a solid surface such as magnetic beads, silica or agarose. Once extracted, the oxidation status of the probe will be read by mass spectrometry.

Example 1

Figure 1B:
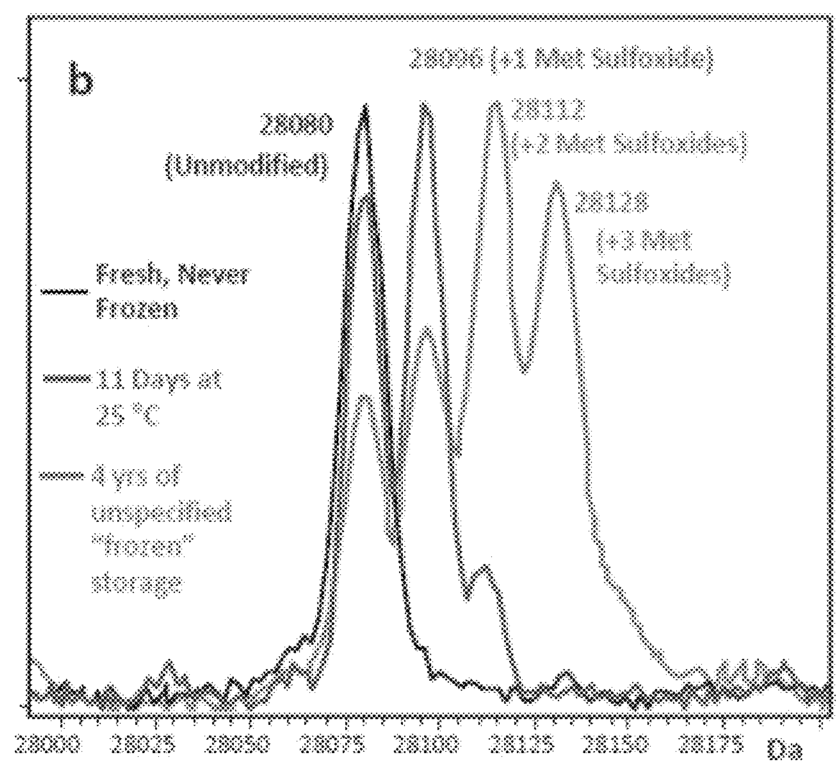

Methods: One half microliter of P/S is diluted into one half milliliter of 0.1% (v/v) trifluoroacetic acid (TFA). Five microliters of this diluted protein solution is then injected onto a liquid chromatograph coupled to an electrospray ionization mass spectrometer. The sample is trapped on a reverse phase column at high aqueous solvent composition. The high aqueous solvent composition is maintained for 3 minutes, resulting in online protein concentration and desalting. The organic solvent composition is then increased to elute the protein from the column into the mass spectrometer. The ion source design of the mass spectrometer is one in which the spray needle is held at ground and the instrument inlet is brought to a high negative potential (for positive ion mode analysis). This design is important because it avoids the possibility of corona discharge and subsequent artefactual protein oxidation during the electrospray process. One run takes approximately 10 minutes. Following application of a charge deconvolution signal processing algorithm to the data, spectra are produced that reveal the relative abundance of the mass variant forms of albumin and apoA-I (FIG. 1).

Our first evaluations demonstrate intra and inter day assay precision for partially oxidized albumin and apoA-I at less than 10% RSD (Relative Standard Deviation) (n>100 and n=15, for albumin and apoA-I respectively). As tested, for EDTA vs. Fluoride-Oxalate anticoagulants, the anticoagulant type does not affect plasma measurements.

Figure 2:
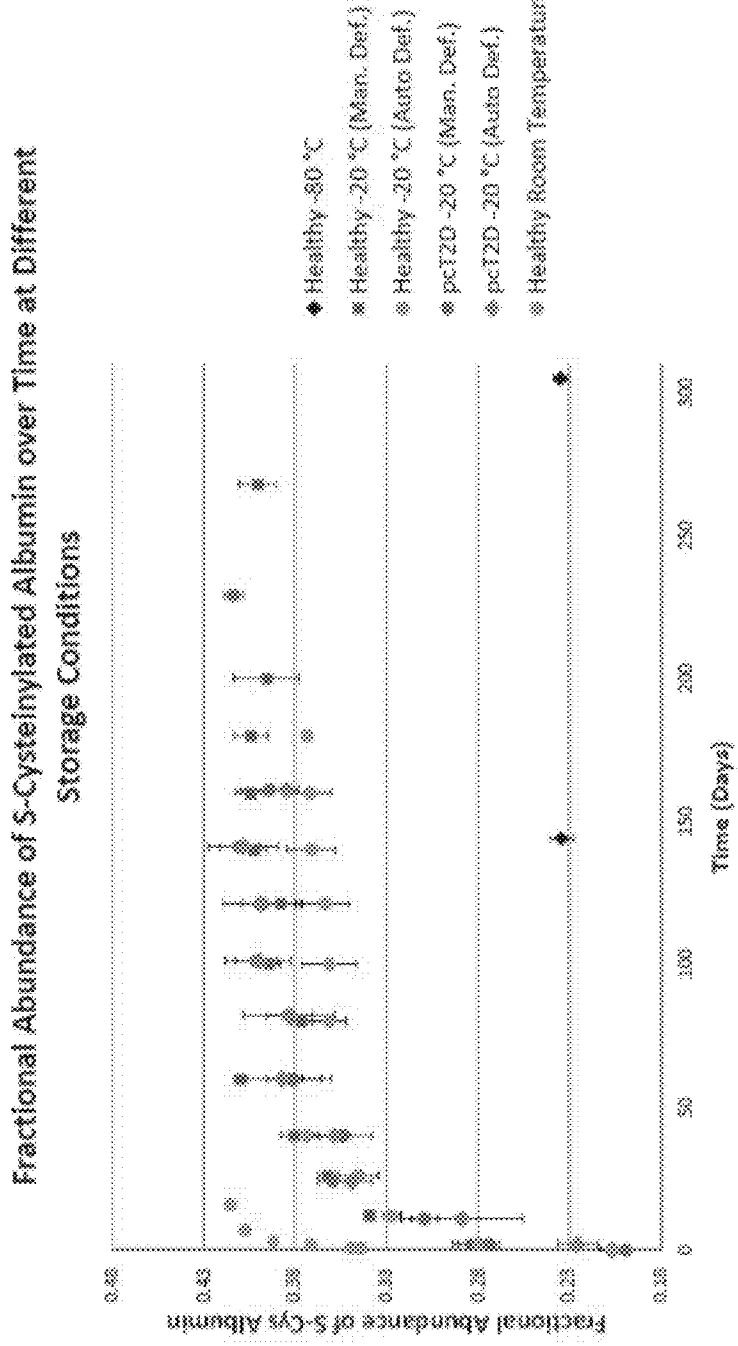
FIG. 2 depicts an increasing abundance of SCA in plasma over time at −80° C., −20° C., and room temperature (25° C.). All samples were collected fresh and started on Day 0 at a fractional abundance of about 0.20. Samples were from a healthy donor and from a poorly controlled type 2 diabetic (pcT2D), stored in either an auto-defrost or manual defrost freezer. Auto-defrost freezers cause sublimation and/or evaporation of P/S water resulting in sample dehydration. Storage in such freezers is not recommended. Shown is the average of 3 aliquots per point (fewer for latter auto defrost freezer points), stored (to no effect) in different types of vials with different headspaces and degrees of sealing. The slight initial increase in the sample stored at −80° C. is likely due to the fact that the sample was measured and then aliquoted. During the aliquoting process the sample was at 4° C.-25° C. for over an hour. The first time point for the room temperature sample was measured at about 17.5 hours.

Marker Characteristics: Oxidized albumin (SCA) begins to accumulate over a period of hours when P/S samples are stored at room temperature (FIG. 2). When P/S samples are stored at −20° C., SCA develops over a period of several days and reaches saturation in less than two months. Albumin appears stable at −80° C. There appears to be no difference in either the starting point or the albumin oxidation rate of plasma from a poorly controlled type 2 diabetic relative to that from a healthy donor (FIG. 2). Likewise, oxidation rates are not significantly affected by whether the −20° C. freezer undergoes automatic defrost cycles or must be manually defrosted. Neither the storage vessel type nor sample storage headspace were found to affect SCA accumulation.

Figure 3:
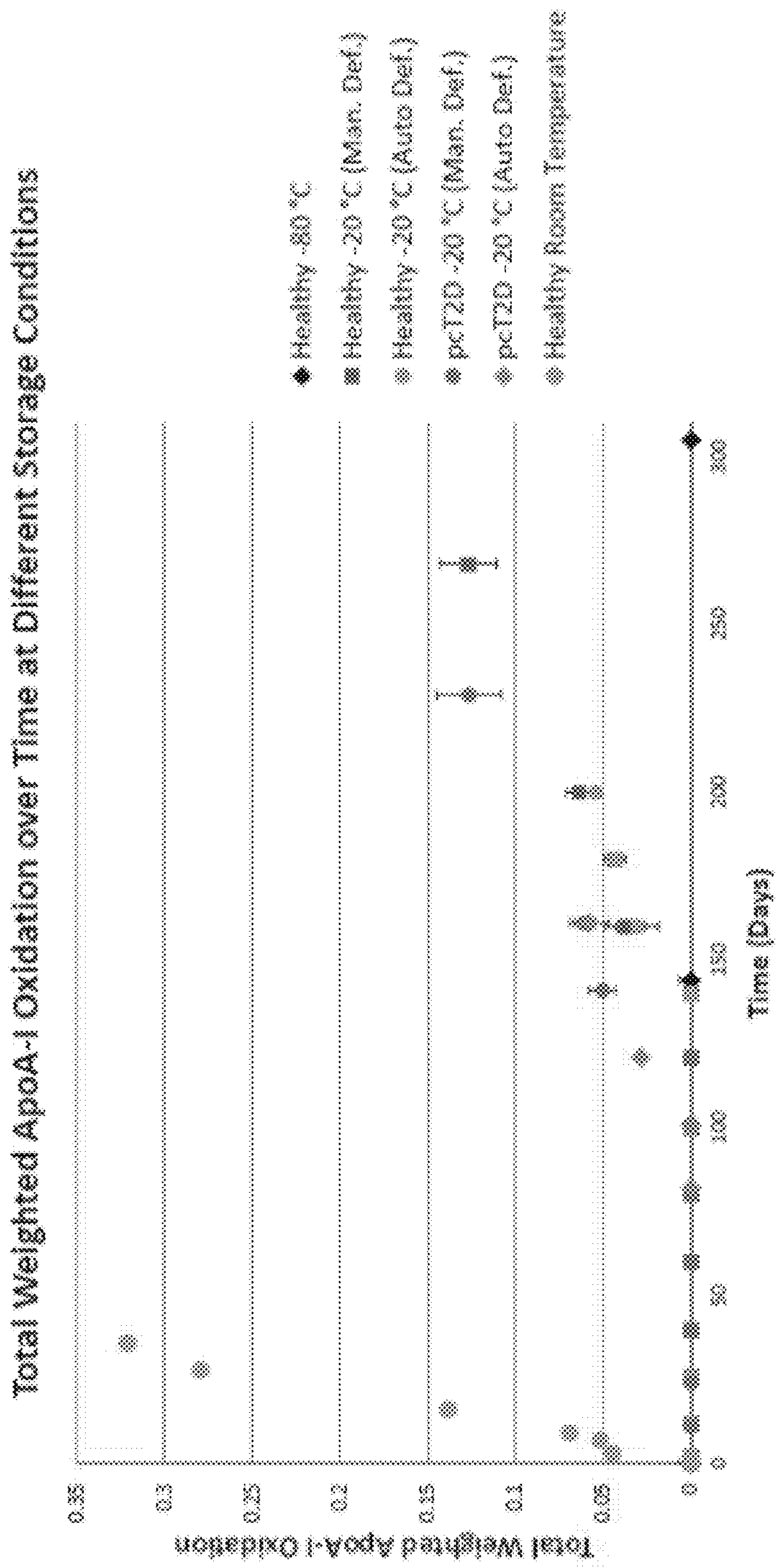
FIG. 3 depicts apolipoprotein A-I oxidation in plasma over time at −80° C., −20° C., and room temperature (25° C.). All samples were collected fresh and started on Day 0 with substantially no oxidation. Since up to 3 oxidation events may occur per apoA-I molecule, data are weighted according the formula: Total weighted MOA1=(0*Native+0.33*SingleOx+0.66*DoubleOx+1*Triple Ox)/Sum of all peak heights Where Native, SingleOx, DoubleOx, and TripleOx are the peak heights of the proteoforms with 0-3 Met sulfoxides, respectively. Thus total weighted MOA1 ranges from about 0 to about 1.

Samples (shown in FIG. 3) were from two healthy donors and from a poorly controlled type 2 diabetic (pcT2D), stored in either an auto-defrost or manual defrost freezer. Auto-defrost freezers cause sublimation and/or evaporation of P/S water resulting in sample dehydration. Storage in such freezers is not recommended. FIG. 3 illustrates the average of 3 aliquots per point (fewer for latter auto defrost freezer points), stored (to no effect) in different types of vials with different headspaces and degrees of sealing. Our first evaluation (n=15) puts intra and interday assay precision for total weighted MOA1 at less than 10% RSD.

ApoA-I oxidizes over a longer time frame than that of albumin. MOA1 begins to accumulate after about one week of P/S storage at room temperature (FIG. 3). At about −20° C. it takes approximately 100-150 days for MOA1 to reach detectable limits. Like albumin, apoA-I appears completely stable at about −80° C. In and of themselves, freeze-thaw cycles do not contribute to albumin or apoA-I oxidation. The changes in SCA that are observed over the course of 12 to 18 freeze-thaw cycles are approximately what would be expected given the total thawed time of the samples (0.27 and 0.28, respectively). ApoA-I did not show any sign of oxidation after 18 freeze-thaw cycles.

When the analytical methods for albumin and apoA-I analysis were first developed, it was hypothesized that physiological oxidative stress was responsible for relative increases in SCA and MOA1. However after further investigation of well characterized samples it has become clear that SCA and MOA1 are not elevated in freshly collected, properly stored samples—regardless of patient health status.

For example, we have documented minimal SCA and no MOA1 in such samples from diabetics and acute coronary syndrome patients (some of which were experiencing a myocardial infarction at the time of sample collection). On the other hand, we have observed severely oxidized albumin and apoA-I in samples from healthy patients that were obtained from a commercial biobank and stored under unspecified "frozen" conditions for 4 years (FIG. 1). SCA and MOA1 may serve as endogenous reference markers of P/S sample integrity, i.e., approximately how oxidized a sample has become relative to a reference sample.

Unless they are measured at collection, however, the initial states of endogenous markers cannot be known with absolute certainty. Likewise, it is possible that the reference ranges for SCA and MOA1 oxidation may be found unsuitable in some patient populations—or they may be unmeasurable in certain rare heterozygous coding region point imitation cases. Yet given the data described above, ex vivo protein oxidation still can be very useful as a means by which to monitor biospecimen, such as plasma or serum, sample integrity.

In an additional embodiment, we have designed peptide-based probes of P/S oxidation based on the oxidative chemistries we have observed in albumin and apoA1 (FIG. 4; Sequence ID No. 1).

At temperatures above the −30° C. freezing point of blood plasma/serum (P/S), proteins and other biomolecules are vulnerable to molecular damage that may adversely impact clinically relevant biomolecular measurements without investigators knowing it. While consuming only 0.5 μL of P/S, it is sensitive enough to robustly detect molecular changes that take place within hours at room temperature or two days at −20° C. (a common laboratory freezer temperature). In initial studies the measurements provided by embodiments herein do not appear to be naturally elevated by patient disease status, including diabetes and advanced heart disease. Methods herein simultaneously detect two different types of biomolecular alteration caused by improper P/S sample storage. One form of alteration is fast-acting, occurring on the order of hours at room temperature and weeks at −20° C. The other form occurs over days at room temperature or several months at −20° C. Neither alteration occurs when samples are stored at −80° C. The mechanisms underlying these alterations are understood to the point where it is possible to link the behavior of target protein(s) of interest to one or both types of measured biomolecular alteration.

A few markers of P/S protein stability are based on empirical changes in measured protein concentration. These include soluble CD40 ligand (sCD40L), MMP-9, VEGF, several interleukins, and MMP-7. About half of these proteins contain at least one free Cys residue and all contain multiple Met residues. In fact, the most labile of these proteins are those with free Cys residue(s) while those with only Met residues (no free Cys) seem to tolerate adverse handling and storage conditions longer. These observations are in accord with our findings on SCA and MOA1, respectively, and suggest that our proteoform-specific markers may be ideally suited as surrogate representatives of the biochemical processes underlying the apparent losses of other candidate markers of P/S stability.

The mechanism behind sample oxidation is understood; embodiments herein are not based on arbitrary "loss" or a paradoxical "increase" of a protein as determined by a univariate (single number output) assay based on molecular interaction e.g., an ELISA assay. Embodiments herein provide direct, mechanism based measurements of molecular damage that occurs as a result of improper plasma/serum sample handling and storage. In essence, it allows users to literally "see" the molecular damage that has occurred (FIG. 1).

Based on data collected in diabetics and acute coronary syndrome patients the reference ranges of our endogenous markers in fresh samples are low and do not appear to be elevated by a patient disease state.

Methods herein are sensitive enough to robustly detect molecular changes that occur within hours at about room temperature or about two days at approximately −20° C. In a preferred embodiment, the method consumes only about 0.5 μL of plasma/serum, making it applicable to any existing cohort of samples without significantly depleting specimen volume. SCA and MOA1 are molecular forms of albumin and apolipoprotein A-I, respectively. Based on our initial research, a relative abundance of SCA above about 30% appears indicative of sample exposure to non-ideal storage conditions. Likewise, an MOA1 relative abundance of greater than 2-3% indicates sample mistreatment.

Figure 5:
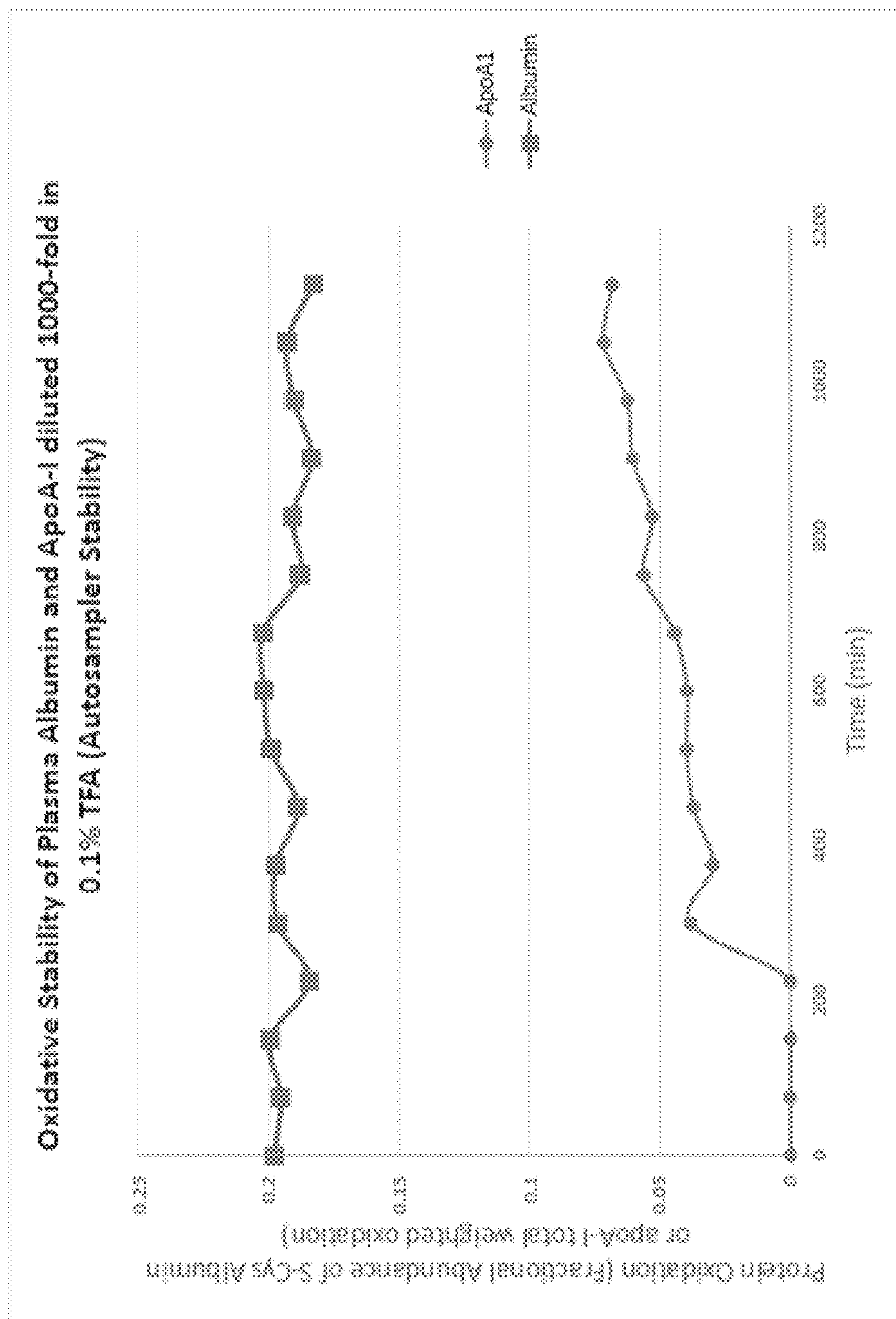
FIG. 5 depicts the oxidative stability of plasma albumin and ApoA-I diluted 1000-fold in 0.1% TFA (Autosampler Stability).

To assess the potential for preparing P/S for walk-away autosampler-based analysis, fresh plasma from a healthy donor was diluted in the usual manner (1000-fold in 0.1% tntluoroacetic acid), aliquoted into a 96-well plate and set in front of the LC-MS autosampler for serial injections (as described above). Albumin S-cysteinylation was stable, but apoA-I oxidation began to develop within about 5 hours (24 injections) (FIG. 5). In previous work (unpublished) we have found that addition of 1 mM MetSer dipeptide can delay for hours the methionine oxidation of other proteins that have been pre-isolated from serum and are present at low concentration in a similarly acidic solution. For apoA-I in diluted plasma, however, 5 mM MetSer was insufficient to prevent oxidation of methionine residues. In consideration of these results, all samples were diluted immediately before injection onto the LC-MS.

Figure 6:
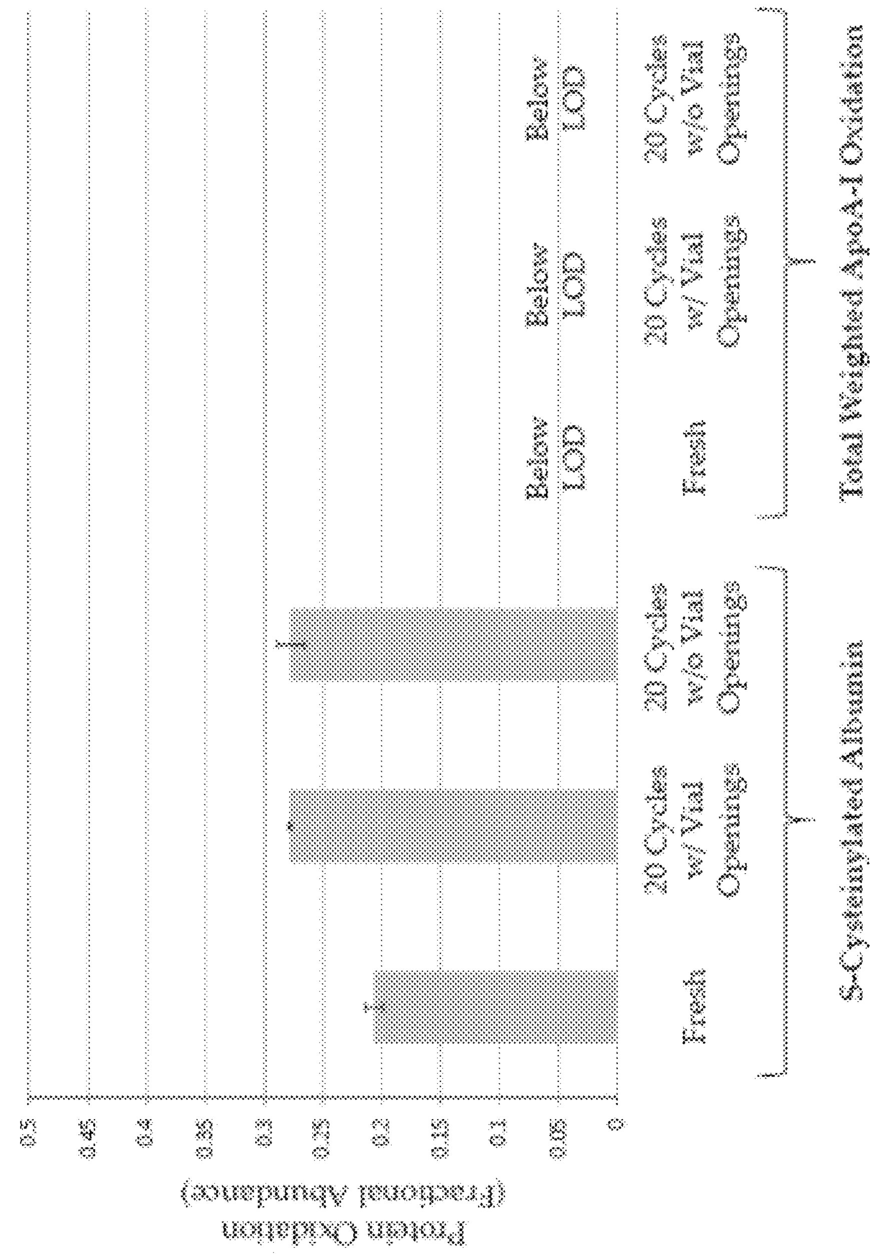
FIG. 6 shows the freeze-thaw effects on oxidized albumin and ApoA-I.

Freeze-thaw cycles are often suspected to contribute to sample instability. To assess the effect of freeze-thaw cycles on albumin and apoA-I oxidation, two 50-μL aliquots from a healthy donor were stored in screw cap vials equipped with a sealing o-ring at −80° C. and subjected to 20 freeze-thaw cycles. The starting fractional abundance of S-cysteinylated albumin was 0.21±0.0071 (n=6 replicates) and there was no evidence of apoA-I oxidation. Each day the samples were thawed at room temperature, immediately mixed, then very briefly centrifuged to remove plasma from the test tube walls and placed back in storage at −80° C. For one of the samples, the cap was briefly removed and then replaced each day prior to re-freezing—a procedure intended to simulate the minimum exposure needed to remove a specimen from the freezer, take an aliquot, and then return it to storage. To determine whether fresh air exposure in addition to freeze-thaw cycles affected albumin or apoA-I oxidation the cap was never removed from the second sample until the final analysis. After twenty such freeze-thaw cycles (and an estimated total thawed time of 300 minutes) the fractional abundance of S-cysteinylated albumin in the repeatedly opened vial had reached 0.28±0.0014 (n=3 replicates) and that in the once-opened vial had reached 0.28±0.012 (n=3 replicates), indicating a small increase in albumin oxidation in accord with total thawed time, but no effect of vial opening and renewed air exposure during each thaw cycle (FIG. 6). No apoA-I oxidation was evident in either sample.

Figure 7:
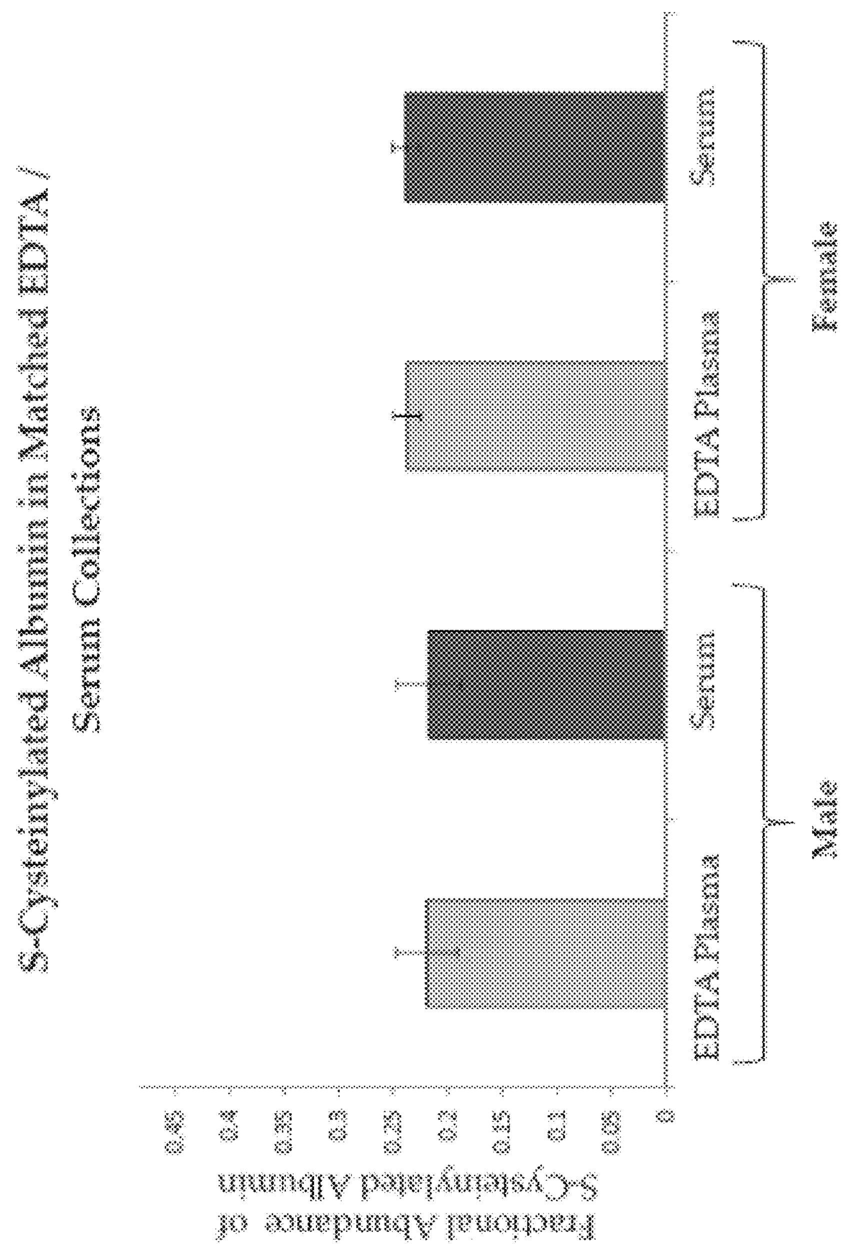
FIG. 7 depicts S-cysteinylated albumin in matched EDTA/serum collections.

Matched EDTA plasma and serum sample sets from 2 healthy males and 2 healthy females were collected fresh to determine whether plasma differs from serum with regard to initial measurements of albumin and apoA-I oxidation. Plasma samples were processed, aliquoted and placed in a −80° C. freezer within 35 minutes of collection; serum samples were placed at −80° C. within 95 minutes of collection. Aliquots were thawed and analyzed in duplicate within four months. Albumin S-cysteinylation was minimal and no differences were evident in its fractional abundance between males and females or between EDTA plasma and serum (FIG. 7). No apoA-I oxidation was evident.

Surface area-to-volume (SAV) ratio effects on albumin and apoA-I oxidation were investigated at room temperature by dividing a fresh plasma sample from a healthy volunteer into 100-μL, 200-μL, and 400-μL aliquots in cylindrical, 8-mm internal diameter polypropylene screw-cap test tubes. Additional 10-μL aliquots were placed into a 1.5 mL conical-bottom polypropylene snap-cap test tube to represent an extreme case of high surface area-to-volume.

Figure 8A:
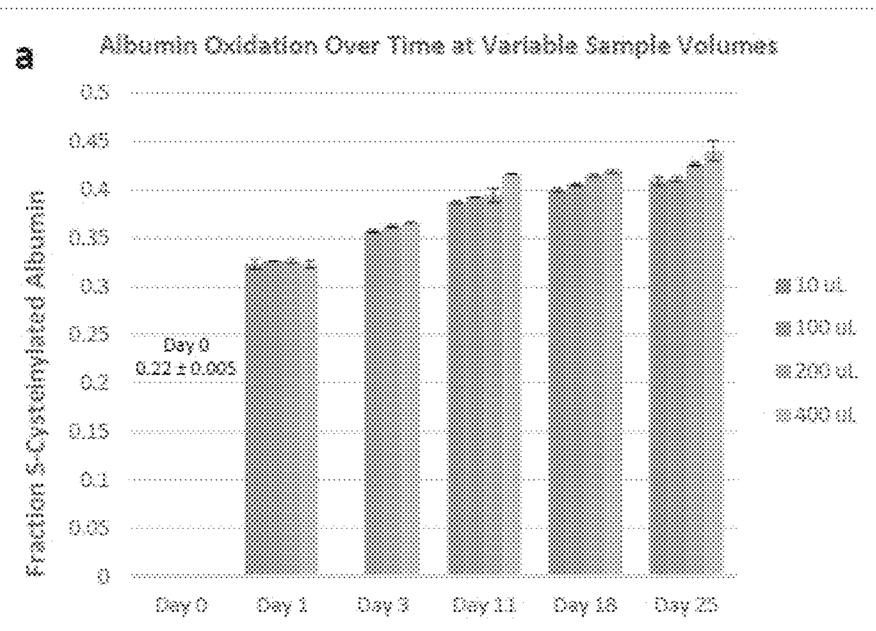
FIGS. 8*a*-8*d* show the surface area-to-volume (SAV) ratio effects on albumin and apoA-I oxidation.
Figure 8B:
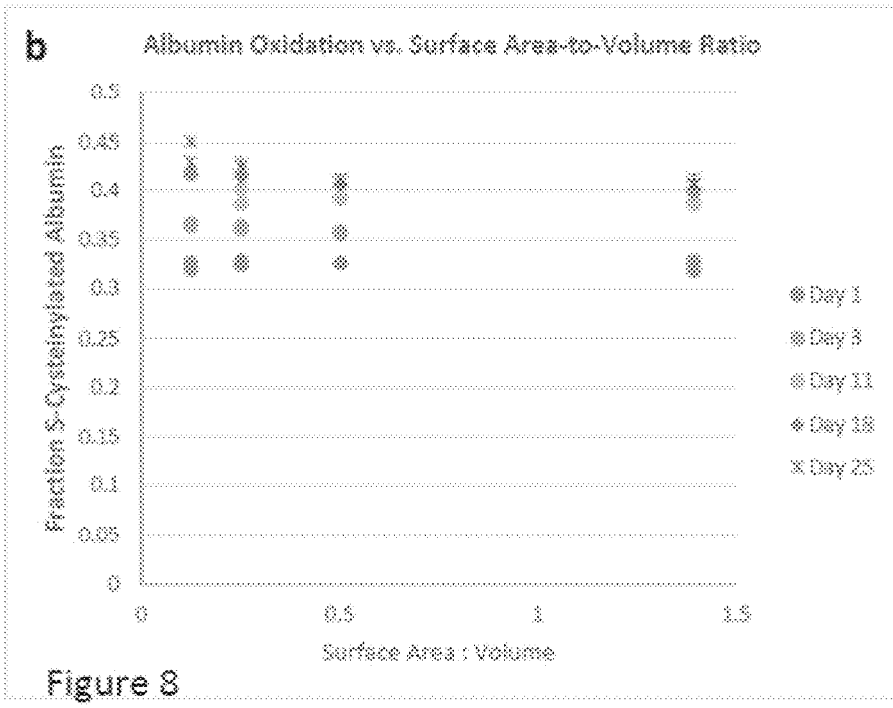
Figure 8C:
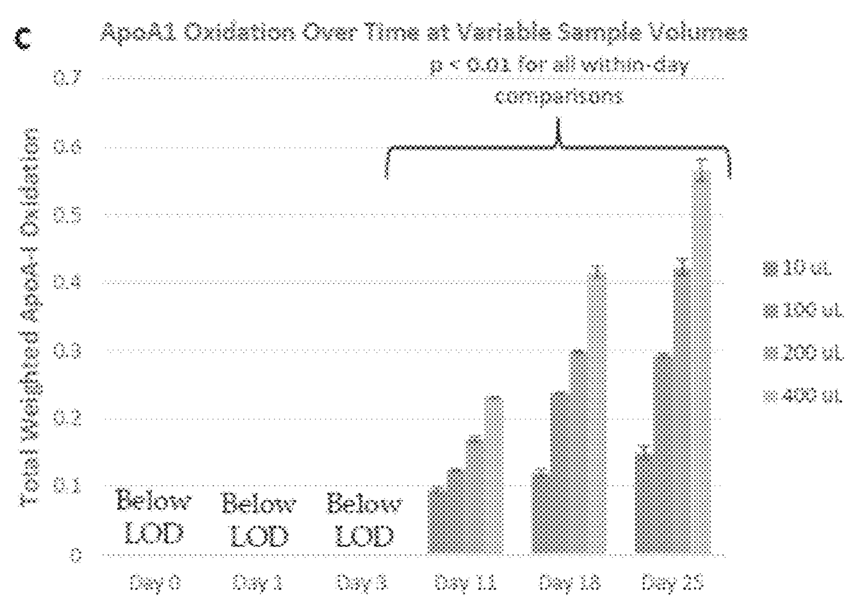
Figure 8D:
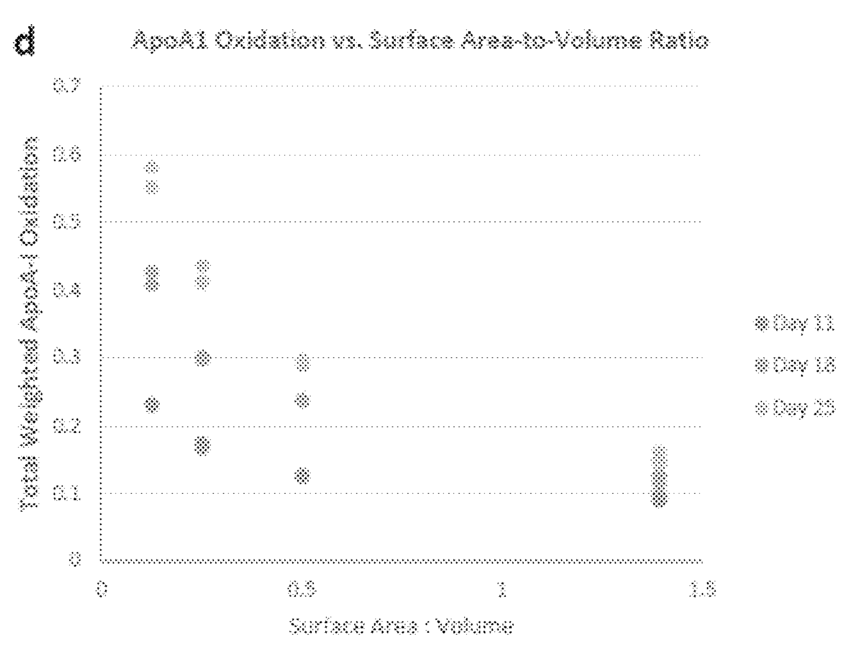

The fraction of S-cysteinylated albumin increased to a maximum of about 0.4 in all samples at a similar same rate—including the 10-μL sample (FIG. 8*a-b*). On the other hand, apoA-I oxidation varied systematically with SAV ratio, but in the opposite direction than expected (FIG. 8*c-d*): Pairwise comparisons of apoA-I oxidation for all SAY ratios were statistically significant on Days 11, 18 and 25 (ANOVA, $p<0.01$ for all Tukey pairwise comparisons). Within each day the Spearman coefficient of determination for apoA-I oxidation vs. SAV ratio was greater than 0.9 ($p<0.001$).

An additional advantage is that a single assay captures information from both a short-term impact (SCA) and a long-term impact (MOA1) marker of oxidative plasma/serum specimen integrity.

Example 2

Biospecimen integrity is critically important when it comes to ensuring the validity of clinically oriented research. Many clinically important P/S biomolecules that serve as biomarkers are unstable ex vivo. A sampling of the ever-expanding list includes numerous cancer and cancer-immunology relevant proteins such as VEGF, IL-1α, IL-1β, IL-10, IL-15, IL-17, IFN-γ, as well as important miRNAs such as miR-21.

Unfortunately, ex vivo storage and handling conditions have the potential to impact measurements of these molecules as much or more than the in vivo (clinical) conditions of interest—which can lead directly to false conclusions in biomedical research This has created an urgent and growing call to minimize ex vivo molecular changes to P/S and to identify those changes when they occur—a need increasingly recognized by top-tier clinical chemistry journals, which have begun to require documentation of biospecimen handling conditions in manuscript submissions.

S-Cys-Alb (FIG. 9) arises as either 1) an oxidative disulfide exchange reaction between the single free thiol-containing cysteine residue within albumin (Cys34) and free cystine (the disulfide dimer of the free amino acid cysteine) in P/S, or 2) as a reaction between Cys34 of albumin and free cysteine in which one of the two thiol groups has been oxidatively converted to a reactive cysteine sulfenic acid intermediate. In other words, a mixture of free-thiol containing protein (such as albumin), cysteine, and cystine exposed to air and unavoidable trace quantities of redox-active transition metals will undergo disulfide exchange and net oxidation—ultimately oxidizing all free thiols into disulfides. Thus if the molar concentration of albumin is greater than the molar equivalents of cysteine (of which cystine contains two), the concentration of S-Cys-Alb will eventually reach a plateau without the fraction of S-Cys-Alb reaching 1. This is what happens in unfrozen P/S where the average concentration of albumin within the human population is 650±60 (SD) that of cysteine is 11±1 (SD) μM and cystine is 70±10 (SD) μM (cf. FIG. 2).

The fact that free cysteine and cystine exist in vivo in all P/S samples allows us to predict that measurement of S-Cys-Alb in fresh P/S samples followed by intentional ex vivo incubation to drive the oxidative S-cysteinylation of albumin to its maximum value should always produce a second S-Cys-Alb value that was higher than the first. Thus by measuring S-Cys-Alb before and after an intentional incubation period that causes S-Cys-Alb to hit its maximum value, the difference between these values, ΔS-Cys-Alb, is readily interpreted as inversely proportional to the degree of ex vivo oxidation that occurred prior to the first measurement of S-Cys-Alb.

Thus, for example, a ΔS-Cys-Alb value of zero would indicate that the original P/S sample had already reached its maximum value of S-Cys-Alb: That is, since free cysteine and cystine are always present in vivo, a lack of change in S-Cys-Alb following an ex vivo incubation to drive S-Cys-Alb to its maximum possible value would indicate that the maximum value of S-Cys-Alb had already been reached by the sample due to extended exposure to thawed conditions.

Because the in vivo reference ranges of albumin, cysteine and cystine are known (see above), it is possible to calculate a ΔS-Cys-Alb range within which 95% of fresh human P/S samples should fall. This range turns out to be 0.14 to 0.36.

In some embodiments, methods for measuring S-Cys-Alb involve 0.5 μL of P/S is diluted into one-half milliliter of 0.1% (v/v) trifluoroacetic acid (TFA). Five microliters of this diluted protein solution is then injected onto a liquid chromatograph coupled to an electrospray ionization mass spectrometer. The sample is trapped on a reverse-phase column at high aqueous solvent composition. The high aqueous solvent composition is maintained for 3 minutes, resulting in online protein concentration and desalting. The organic solvent composition is then increased to elute the protein from the column into the mass spectrometer. The ion source design of the mass spectrometer is one in which the spray needle is held at ground and the instrument inlet is brought to a high negative potential (for positive ion mode analysis).

Figure 9:
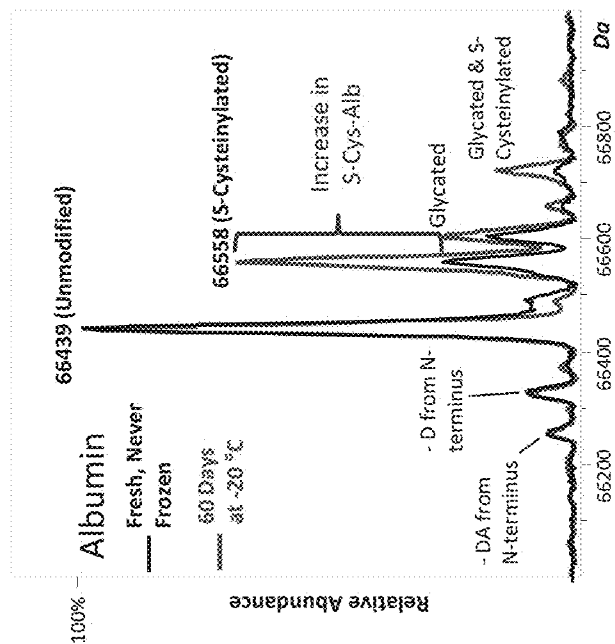
FIG. 9 depicts charge-deconvoluted ESI mass spectra of albumin from a healthy donor showing increased oxidation (S-cysteinylation) under less-than-ideal storage conditions. Black spectrum: Fresh, never frozen. Red spectrum: Same sample, aged for 60 days at −20° C. The quantitative difference in the relative abundance of the S-cysteinylated form of albumin before and after an overnight incubation at 37° C. that drives this peak to its maximum height constitutes ΔS-Cys-Albumin.

This design is important because it avoids the possibility of corona discharge and subsequent artefactual protein oxidation during the electrospray process. One run takes approximately 10 minutes. Following application of a charge deconvolution signal processing algorithm to the data, spectra are produced that reveal the relative abundance of the native and S-cysteinylated forms of albumin (FIG. 9). Our prior results indicate that intra and interday assay precision for S-Cys-Alb is less than 7% RSD and there is no significant difference in S-Cys-Alb in fresh EDTA plasma vs. fresh serum. Accordingly, once P/S is diluted in 0.1% TFA, S-Cys-Alb is stable enough to allow up to 96 samples to be queued for automated injection via an autosampler.

Figure 10:
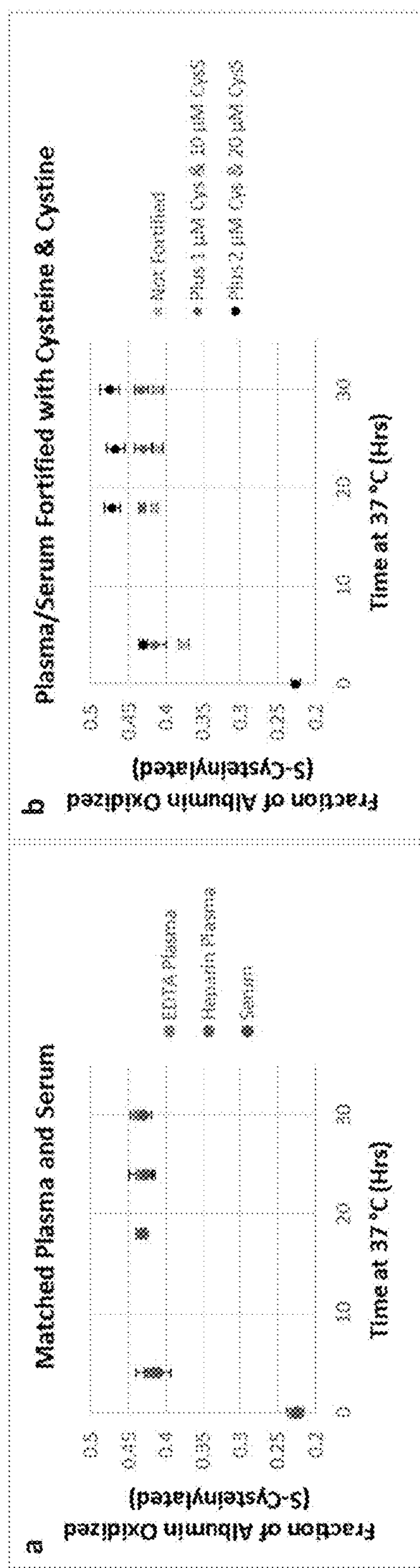
FIGS. 10*a* and 10*b* show a determination of incubation conditions needed to maximize albumin oxidation (S-Cys-Alb). Matched EDTA plasma, heparin plasma and serum were collected from a male volunteer. We have previously determined that there is no difference between either plasma or serum in a comparison of males vs. females. Three 10 μL aliquots of each P/S type were placed into 0.5 mL snap cap test tubes, which were then incubated in a humidified oven at 37° C. for the times indicated (a). No significant differences were noted between P/S sample types; in each case albumin oxidation (S-Cys-Alb) reached a maximum after 18 hr sat 37° C. To simulate variability exhibited in the P/S concentration of cysteine (Cys) and cystine (CysS) within the general population, samples were fortified with either 1 μM Cys+10 μM CysS (i.e., 1 SD of the population reference range) or 2 μM Cys+20 μM CysS (i.e., 2 SD of the population reference range) and the experiment was repeated (b). Each point is the average of 3 EDTA plasma, 3 heparin plasma and 3 serum aliquots. Increased concentrations of Cys and CysS clearly raise the maximum fraction of oxidized albumin (S-Cys-Alb) as expected, but do not alter the time frame in which the maximum plateau is reached. All error bars represent standard deviation.

The ex vivo incubation conditions required to drive S-Cys-Alb to its maximum value in any given P/S sample is 16-18 hrs at 37° C. (for 9 μL of P/S in a sealed test tube)—see FIG. 10. Following this incubation period, S-Cys-Alb is re-measured in the sample and the difference between the first and last measurements is taken as ΔS-Cys-Alb.

Figure 11:
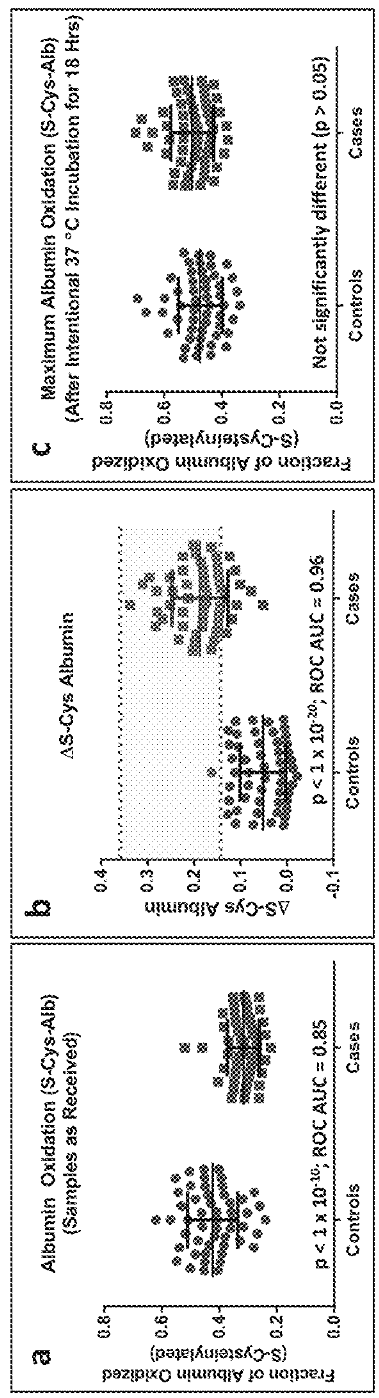
FIGS. 11*a*-11*c* depict the ability of S-Cys-Alb (a) and enhanced ability of ΔS-Cys-Alb (b) to detect sample integrity discrepancies in highly pedigreed serum samples collected, handled and stored under the same SOP. Yellow highlighted range indicates the theoretical/calculated range that should be observed in pristine samples based on the known reference ranges of albumin, cysteine and cystine found in 95% of human P/S samples; samples that lie below this range are either two standard deviations outside of the average human reference range or (more likely) have experienced ex vivo oxidation from exposure to the thawed state that must have occurred prior to the first measurement of S-Cys Alb. Panel (c) demonstrates a lack of difference between the two sample sets with regard to the maximum degree to which albumin can be S-cysteinylated (oxidized) via ex vivo incubation for 18 hrsat 37° C. n=52 controls and n=52 cases.

To further test the utility of ΔS-Cys-Alb as a marker of P/S integrity, the assay was applied to a set of 52 stage I lung adenocarcinoma cases and 52 age/gender/smoking matched controls that were collected under the same standard operating procedure as part of a National Cancer Institute-sponsored research program. Based on the then-known histories of the samples, there should have been no differences in either the initial measurements of S-Cys-Alb or in ΔS-Cys-Alb between the cases and the controls. Interestingly, however, for both S-Cys-Alb and ΔS-Cys-Alb there were significant differences between the case and control samples: The receiver operating characteristic area under the curve (c-statistic) for S-Cys-Alb was 0.85; for ΔS-Cys-Alb this metric of separation between the groups was increased to 0.96 (FIG. 11).

Notably, there was no significant difference between the two groups with regard to the maximum value of S-Cys-Alb following the intentional ex vivo incubation at 37° C. (FIG. 11*c*). Moreover, the vast majority of the lung cancer samples had ΔS-Cys-Alb values that were perfectly in-line with the predicted population reference range for ΔS-Cys-Alb in freshly collected samples (FIG. 11*b*).

Figure 12:
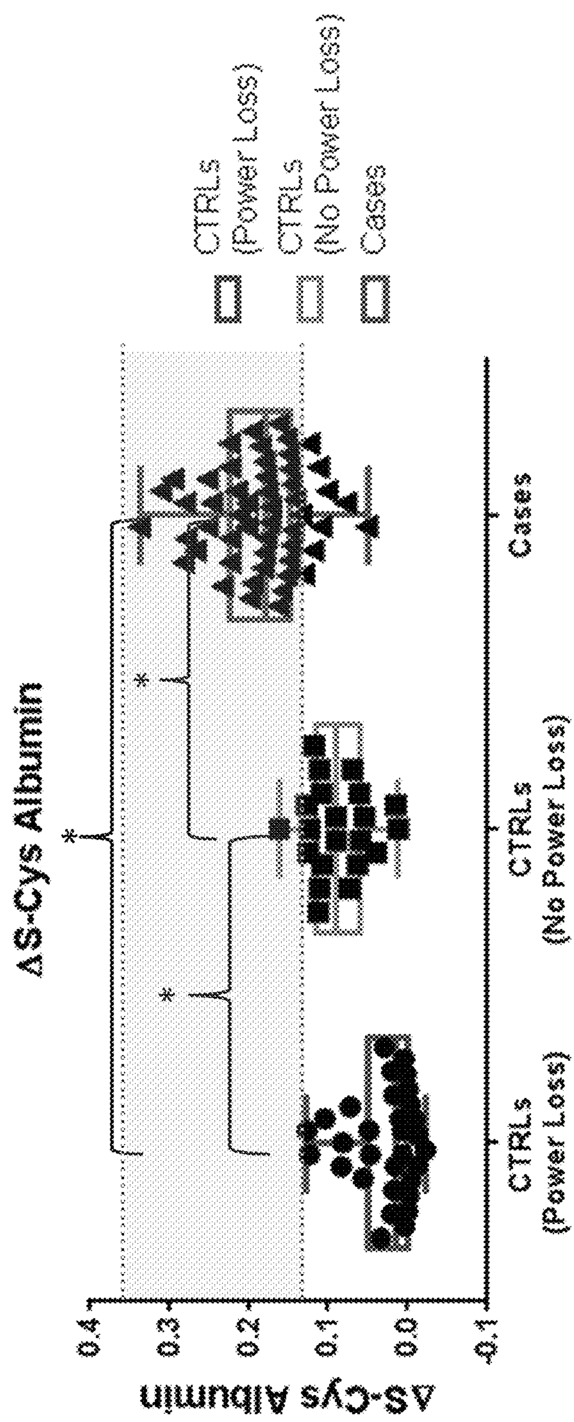
FIG. 12 shows a detailed breakdown of FIG. 11*b*. ΔS-Cys Albumin in control specimens that lost −80° C. freezer power for 2-3 days (left), control specimens that did not lose power (middle), and in stage I lung adenocarcinoma (Case) samples (right). In total, 52 CTRL samples and 52 Case samples were analyzed. Control samples are grouped as having been collected before (n=31) and after (n=21) a natural disaster. The yellow highlighted range indicates the theoretical/calculated range that should be observed in pristine samples based on the known reference ranges of albumin cysteine and cystine found in 95% of human plasma/serum samples. The reason for the significant difference between the "No Power Loss" CTRLs and the cases is not known but it should be noted that ΔS-Cys Albumin is not a biomarker of stage I lung adenocarcimona. *$p<0.05$ for Dunn's multiple comparison test following non-parametric ANOVA. ROC c-statistic for Power Loss vs. No Power Loss CTRLs=0.85.

Though previously undisclosed by the specimen provider, further investigation revealed that the −80° C. freezers containing most of the control specimens had experienced a 2-3 day loss of power during a natural disaster. Moreover, the particular control samples that experienced the temporary increase in temperature had significantly lower ΔS-Cys-Alb values than the residual control samples that did not experience the power outage (FIG. 12). Thus the ΔS-Cys-Alb assay identified damaged P/S samples within a highly pedigreed set of specimens for which there had originally been no concern about potential integrity issues.

The following claims are not intended to be limited to the materials and methods, embodiments, and examples described herein.

The invention claimed is:

1. A method for assessing ex vivo oxidation of a stored biospecimen sample, comprising:

measuring protein oxidation of at least one of an albumin and apolipoprotein A-1 (apoA-1) in said stored biospecimen sample;

measuring protein oxidation of at least one of an albumin and apolipoprotein A-1 (apoA-1) in a portion of said stored biospecimen sample intentionally incubated to cause oxidation to hit its maximum value;

quantifying a difference in protein oxidation of said at least one of an albumin and apolipoprotein A-1 (apoA-1) of said stored biospecimen sample in comparison to protein oxidation of at least one of an albumin and apolipoprotein A-1 (apoA-1) in said portion of said stored biospecimen sample intentionally incubated to cause oxidation to hit its maximum value, wherein said difference in a level of oxidation in the stored biospecimen sample and said portion of the stored biospecimen sample is inversely proportional to a degree of ex vivo oxidation.

2. The method of claim 1, wherein said measuring is performed via electrospray ionization mass spectrometry.

3. The method of claim 1, wherein said biospecimen is blood plasma or serum.

4. The method of claim 1, wherein said measuring comprises measuring an amount of S-cysteinylation of albumin.

5. A method for assessing oxidation of a stored biospecimen sample comprising:

quantifying an amount of protein oxidation of at least one of an albumin and apolipoprotein A-1 (apoA-1) in said stored biospecimen sample;

quantifying an amount of protein oxidation of at least one of an albumin and apolipoprotein A-1 (apoA-1) in a portion of said stored biospecimen sample intentionally incubated to cause oxidation to hit its maximum value; and comparing said amount of protein oxidation of at least one of an albumin and apolipoprotein A-1 (apoA-1) in said stored biospecimen sample to that of the portion of said stored biospecimen sample intentionally incubated to cause oxidation to hit its maximum value, wherein a difference in a level of oxidation in the stored biospecimen sample and said portion of the stored biospecimen sample is inversely proportional to a degree of oxidation.

6. The method of claim 5, wherein said quantifying is performed via electrospray ionization mass spectrometry.

7. The method of claim 6, wherein said biospecimen is blood plasma or serum.

8. The method of claim 6, wherein said quantifying comprises measuring an amount of S-cysteinylation of albumin.

* * * * *